(12) United States Patent
Ohtsuka et al.

(10) Patent No.: US 8,338,027 B2
(45) Date of Patent: Dec. 25, 2012

(54) PHENANTHRENEQUINONE COMPOUND, ELECTRODE ACTIVE MATERIAL, AND POWER STORAGE DEVICE

(75) Inventors: Yu Ohtsuka, Osaka (JP); Junichi Yoshida, Osaka (JP); Toshiki Nokami, Kyoto (JP)

(73) Assignee: Panasonic Corporation, Osaka (JP)

( * ) Notice: Subject to any disclaimer, the term of this patent is extended or adjusted under 35 U.S.C. 154(b) by 141 days.

(21) Appl. No.: 12/530,382

(22) PCT Filed: Mar. 7, 2008

(86) PCT No.: PCT/JP2008/000492
§ 371 (c)(1),
(2), (4) Date: Sep. 8, 2009

(87) PCT Pub. No.: WO2008/108105
PCT Pub. Date: Sep. 12, 2008

(65) Prior Publication Data
US 2010/0047688 A1    Feb. 25, 2010

(30) Foreign Application Priority Data
Mar. 8, 2007 (JP) .................................. 2007-058896

(51) Int. Cl.
*H01M 4/60* (2006.01)
(52) U.S. Cl. ...................... 429/213; 552/292; 568/714
(58) Field of Classification Search ................. 552/292; 568/714; 429/213
See application file for complete search history.

(56) References Cited

U.S. PATENT DOCUMENTS

| | | | |
|---|---|---|---|
| 4,343,871 A | 8/1982 | Tobishima et al. | |
| 6,274,268 B1 | 8/2001 | Fujiwara et al. | |

FOREIGN PATENT DOCUMENTS

| | | |
|---|---|---|
| EP | 0924782 A1 | 6/1999 |
| EP | 0 971 426 A2 | 1/2000 |
| EP | 1713101 A1 | 10/2006 |
| JP | 56-086466 | 7/1981 |
| JP | 04-087258 | 3/1992 |
| JP | 06-211757 | 8/1994 |
| JP | 10-154512 | 6/1998 |
| JP | 10-289617 | 10/1998 |
| JP | 2000-030710 | 1/2000 |
| JP | 2000-082467 | 3/2000 |
| JP | 2005-019775 | 1/2005 |
| JP | 2006-048974 A | 2/2006 |
| JP | 2006-213634 | 8/2006 |
| JP | 2006-352000 | 12/2006 |
| JP | 2007-187728 | 7/2007 |
| JP | 2007-305430 | 11/2007 |
| WO | WO 2006/097419 A1 | 9/2006 |

OTHER PUBLICATIONS

Japanese Notification of Reasons for Refusal issued in Japanese Patent Application No. JP 2007-058896, dated Jun. 25, 2009.
Britta N. Boden et al., "Tetraalkoxyphenanthrene: A New Precursor for Luminescent Conjugated Polymers," Organic Letters, 2006, vol. 8, No. 9, pp. 1855-1858.
European Search Report issued in European Patent Application No. 08720378.2 dated Jun. 4, 2012.

*Primary Examiner* — Ula C Ruddock
*Assistant Examiner* — Frank Chernow
(74) *Attorney, Agent, or Firm* — McDermott Will & Emery LLP

(57) ABSTRACT

Disclosed is a novel organic compound synthesized by oligomerizing or polymerizing a specific quinone compound having two quinone groups at the ortho position and having a property such that the electron transfer occurs associated with a reversible redox reaction, the organic compound being insoluble in an organic solvent and having a high energy density, and thus being useful as an electrode active material for a power storage device. Using this organic compound as an electrode active material can improve the energy density, reduce the weight and size, and improve the functionality of the power storage device.

5 Claims, 3 Drawing Sheets

PHENANTHRENEQUINONE COMPOUND, ELECTRODE ACTIVE MATERIAL, AND POWER STORAGE DEVICE

RELATED APPLICATIONS

This application is the U.S. National Phase under 35 U.S.C. §371 of International Application No. PCT/JP2008/000492, filed on Mar. 7, 2008, which in turn claims the benefit of Japanese Application No. 2007-058896, filed on Mar. 8, 2007, the disclosures of which Applications are incorporated by reference herein.

TECHNICAL FIELD

The present invention relates phenanthrenequinone compounds, electrode active materials, and power storage devices. More specifically, the present invention mainly relates to improvement of electrode active materials.

BACKGROUND ART

The recent advancement in electronic technology has led to a remarkable proliferation of portable electronic equipment, such as cellular phones, portable personal computers, personal data assistances (PDAs), and portable game machines. With such a proliferation, there has been an increasing demand for power storage devices, such as secondary batteries capable of being repeatedly charged and discharged, the power storage devices serving as power sources for portable electronic equipment. Among such power storage devices, lithium ion secondary batteries using lithium ions as a mobile carrier have been widely used as power sources for portable electronic equipment, because lithium ion secondary batteries have high electromotive forces and high energy densities and the reduction in size thereof is comparatively easy.

In making portable electronic equipment more widely available, further improvement in performance of the portable electronic equipment has been required, in which there have been important technical problems to be solved, for example, reduction in weight and size, improvement in functionality, and the like. In order to solve these technical problems, it has been required for the batteries serving as power sources, for example, to have an improved energy density. One most possible method for improving the energy density of a battery is a method of using an electrode active material having a high energy density. Under these circumstances, active researches and developments on a novel electrode active material having a high energy density have been conducted, regardless of whether the active material is for a positive electrode or a negative electrode.

For example, there has been examined a utilization as an electrode active material of an organic compound having a property such that the electron transfer occurs associated with a reversible redox reaction. Organic compounds have specific gravities of about 1 $g/cm^3$, and are lighter in weight than inorganic oxides such as lithium cobalt oxide, which have been conventionally used as an electrode active material. However, organic compounds, in particular, organic compounds having low molecular weights, are easy to dissolve in organic solvents, and therefore, it has been impossible to use such organic compounds as an electrode active material for use in the currently widely available lithium secondary batteries.

This is attributable to the fact that a non-aqueous electrolyte prepared by dissolving a supporting salt in a non-aqueous solvent being an organic solvent is a mainstream electrolyte of lithium secondary batteries. If an organic compound is dissolved in the non-aqueous solvent, the electron conductivity between a current collector and the organic compound serving as the electrode active material becomes insufficient, and the reactivity is reduced. Moreover, if the organic compound serving as the electrode active material leaches into the non-aqueous solvent, the concentration of the electrode active material capable of being involved in a redox reaction is reduced, and thus the battery capacity is reduced.

As a solution for this, various proposals have been made, suggesting polymerizing the organic compound serving as the electrode active material, using the electrolyte in the form of solid, and the like. For example, there have been numerous proposals that suggest using as the electrode active material an electrically conductive polymer compound in which the whole molecule is covered with conjugated electron clouds, such as polythiophene, polyaniline, and polypyrrole. However, the problem is that the number of reaction electrons in such a conductive polymer compound is as small as about 0.5. From the fact that the energy density of the electrode active material increases in proportion to the number of reaction electrons, it is clear that such a conductive polymer compound fails to have a sufficient energy density.

The reason why the number of reaction electrons is small is described below by taking polythiophene as an example. Polythiophene has a molecular structure in which thiophene rings are adjacent to one another. It is considered theoretically that per one thiophene ring, a reaction involving an exchange of one electron occurs, that is, a one-electron reaction occurs. However, in polythiophene, which is in an electrically charged state as a result of being involved in a redox reaction, due to the electronic repulsion between the adjacent thiophene rings, the reaction that actually occurs involves an exchange of only about 0.5 electrons. Such electronic repulsion is produced similarly in polyaniline and polypyrrole.

In view of the problems of the conventional conductive polymer compounds, for example, one proposal suggests using a conductive polymer compound prepared by introducing a redox-active quinone functional group into the molecule of polyaniline, as a positive electrode active material for a secondary battery (see, e.g., Patent Document 1). The conductive polymer compound of Patent Document 1 is produced, for example, through polymerization of aminobenzenes having two quinone functional groups at the meta position or the ortho position.

The technique of Patent Document 1 intends to increase the number of reaction electrons by introducing a quinone functional group, which permits two-electron reaction involving an exchange of two electrons, into polyaniline being the conductive polymer compound in which the number of reaction electrons is small. However, in terms of the whole conductive polymer compound of Patent Document 1, the number of reaction electrons is averaged and the actual number of reaction electrons is less than two. In other words, in using a compound having a quinone functional group as the electrode active material in order to improve the energy density of a battery, the technique of Patent Document 1 fails to fully utilize the 2-electron reaction, which is the most advantageous feature of the quinone functional group.

Another proposal suggests a composite electrode for a battery including a quinone compound and a nitrogen-containing polymer compound in combination as an electrode active material (see, e.g., Patent Document 2). The technique of Patent Document 2 utilizes that the quinone compound and the nitrogen-containing polymer compound are bound by intermolecular hydrogen bonding, in order to immobilize the quinone compound on the nitrogen-containing polymer compound and form a composite electrode active material having a high energy density. Further, since the reversibility of reaction of the quinone compound with lithium ions is poor, in order to compensate the poor reversibility, an electrolyte containing protons or having proton conductivity is used, so that only protons are involved in the electron transfer associated with the redox reaction of the composite electrode active material. Here, the quinone compound is exemplified by naphthoquinone, anthraquinone, and the like. The nitrogen-containing polymer compound is exemplified by polyaniline, polypyridine, polypyrimidine, and the like.

However, when an electrode including the composite electrode active material of Patent Document 2 is used in a high-voltage design lithium secondary battery including a counter electrode capable of charging and discharging lithium ions, and an electrolyte being a non-aqueous electrolyte solution, the electric potential difference between the positive electrode and the negative electrode is unlikely to exceed 1.2 V, and therefore, the improvement in the energy density of a battery cannot be reliably achieved. This is probably because the electrode active material is synthesized as a composite material by utilizing hydrogen bonding. Since the current lithium secondary batteries are required to have an electric potential difference of much greater 1.2 V between the positive electrode and the negative electrode, the composite electrode active material of Patent Document 2 is lacking in practicality.

Yet another proposal suggests, as an example of an organic compound synthesized by using 9,10-phenanthrenequinone as a starting compound, a 9,10-bis(N,N-diarylamino)phenanthrene derivative (see, e.g., Patent Document 3). The phenanthrene derivative of Patent Document 3, which is used as an electric charge transporting material of an electrophotographic photosensitive body, is devoid of a ketone group and is a monomer that is soluble in an organic solvent, and therefore, is difficult to use as the electrode active material as it is.

Still another proposal suggests a phenanthrenequinone compound in which one of the two oxo groups in 9,10-phenanthrenequinone is replaced with two phenol groups (see, e.g., Patent Document 4). Patent Document 4 simply discloses that this phenanthrenequinone compound can be used as a raw material of resin materials, resist materials, and the like. This phenanthrenequinone compound is also a monomer that is soluble in an organic solvent.

On the other hand, in view of the fluorescence property of phenanthrenequinone compounds, one report suggests utilizing the phenanthrenequinone compounds as organic electroluminescence materials or chemical sensors (see, e.g., Non-Patent Document 1). This report examines polymer substances synthesized by incorporating phenanthrenequinone compounds and sites such as phenol thereinto, which, however, are also polymer substances that are soluble in an organic solvent.

Patent Document 1: Japanese Laid-Open Patent Publication No. Hei 10-154512
Patent Document 2: Japanese Laid-Open Patent Publication No. 2000-82467
Patent Document 3: Japanese Laid-Open Patent Publication No. Hei 6-211757
Patent Document 4: Japanese Laid-Open Patent Publication No. 2006-213634
Non-Patent Document 1: Organic Letters, 2006, Vol. 8, No. 9, 1855-1858

DISCLOSURE OF THE INVENTION

Problem to be Solved by the Invention

The present invention intends to provide an organic compound that has a high energy density, and is hard to dissolve in an organic solvent, capable of being utilized in reducing the weight and size and improving the functionality of a power storage device, and is useful as an electrode active material; an electrode active material including the organic compound; and a power storage device including the electrode active material.

Means for Solving the Problem

The present inventors have paid attention to the conventional quinone compounds in the course of their study for solving the above-discussed problems. Conventionally, a quinone compound having ketone groups at the para position has been mainly used (hereinafter referred to as a "para-quinone compound"). The ketone groups act as a reaction site in the para-quinone compound, and the ketone groups have a minus charge. The redox reaction between the para-quinone compound and a mobile carrier having a plus charge (hereinafter simply referred to as a "mobile carrier"), when lithium ions are taken as an example of the mobile carrier, will be a two-step reaction comprising the steps of (a) and (b) as shown in the following reaction process formula 1.

Reaction process formula 1

[Chemical formula 1]

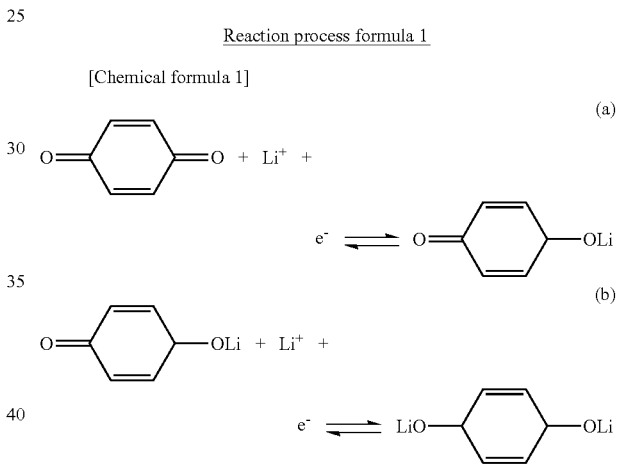

In this two-step reaction, the bonding strength between the ketone groups in the para-quinone compound and the lithium ions are dependent on the difference between the electric charge density of the ketone groups (i.e., the minus charge) and the electric charge density of the lithium ions (i.e., the plus charge). In other words, the bond formed between substances whose charge densities are significantly different from each other becomes more stable and stronger; and the bond formed between substances whose charge densities are both small is low in strength and easily dissociated. In the para-quinone compound, the two ketone groups are present such that one ketone group is away from the other, and the electric charge distribution is localized. As such, the para-quinone compound have a large charge density, and therefore, the difference in charge density from the lithium ions is significantly large.

For this reason, the bond formed through oxidation reaction between the ketone groups and the lithium ions is an extremely strong bond similar to a covalent bond, and thus an energetically stable state is formed. As such, the lithium ions are not easily dissociated from the foregoing bond through reduction reaction. Accordingly, if lithium ions are used as a mobile carrier in the case of using a para-quinone compound as the electrode active material, the reaction reversibility is in turn reduced. The stable state as mentioned here means a strongly bound state from which lithium ions cannot be dissociated through battery reaction, and does not mean the stability of the compound during battery reaction.

Further, in the para-quinone compound, the ketone groups are present such that one ketone group is away from the other, each of the reactions of (a) and (b) independently have an energy level. Specifically, the difference between the electric potential of the first step (the first electron) and the electric potential of the second step (the second electron) is as large as about 1.0 V. The operating voltage and the energy density of a power storage device are calculated from the average of the electric potentials of respective reactions (average voltage). Accordingly, in the case where the electric potential of the second-step reaction is low, the average voltage is lowered, which is not preferable in order to improve the energy density. Moreover, in this case, there is a large difference in electric potential between the two reactions, which is also not preferable in order to control the operation of the power storage device.

On the basis of the above findings, the present inventors continued their studies under the hypothesis that an organic compound which is capable of a redox reaction and has an electric charge density whose difference from that of lithium ions is small would be able to establish a highly reversible redox reaction system, even when lithium ions are used as a mobile carrier. As a result, they have found that a quinone compound having two ketone groups at the ortho position (hereinafter referred to as an "ortho-quinone compound") is adequate for the purpose.

The ortho-quinone compound, similar to the para-quinone compound, when reacting with a mobile carrier, permits two-electron reaction to proceed in two steps. Further, in the ortho-quinone compound, the ketone groups having a minus charge are present such that they are adjacent to each other, and the electric charge distribution is delocalized, lowering the charge density. As such, even when lithium ions are used as a mobile carrier, a bond from which lithium ions can be dissociated by reduction reaction is formed, improving the reaction reversibility. By enabling the use of lithium ions as a mobile carrier, a power storage device having a high output voltage can be provided.

Specifically, a power storage device having a 3 V-class high output voltage can be provided. Furthermore, the electron state formed in the ortho-quinone compound is such that the two ketone groups acting as a reaction site have very approximate energy levels. This means that the reaction potentials in the respective reactions in the 2-electron reaction are approximate to each other, and therefore, there is little or no reduction in the average voltage. As such, the energy density of a power storage device can be improved, and the controllability can also be improved.

It should be noted that, as in the conventional technique, if protons are used instead of lithium ions as a mobile carrier, since a bond similar to an ionic bond is formed through oxidation reaction, protons can be comparatively easily dissociated from the bond through reduction reaction. Consequently, the reaction reversibility is favorable. In this case, however, it is necessary to use a proton-based solvent, and for this reason, due to the restriction of the hydrogen gas generation potential, the electric potential difference between the positive electrode and the negative electrode is unlikely to exceed 1.2 V. In short, even though good reaction reversibility can be obtained, it is difficult to realize a power storage device having a 3.0 V-class high voltage.

In addition, the present inventors have found that by oligomerizing or polymerizing a specific ortho-quinone compound to make it insoluble in an organic solvent, an organic compound is useful as an electrode active material in a power storage device and the like. The inventors have finally found that in the foregoing organic compound, the delocalization property of the electric charge distribution of the original ortho-quinone compound is maintained, the number of reaction electrons is not decreased, and the 2-electron reaction having almost the same energy levels is reliably enabled, and have completed the present invention.

Specifically, the present invention provides a phenanthrenequinone compound represented by the following general formula (1) (hereinafter referred to as a "phenanthrenequinone compound (1)").

[Chemical formula 2]

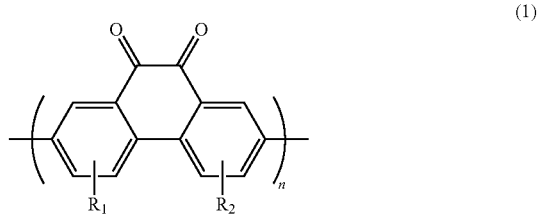

(1)

In the formula, $R_1$ and $R_2$ are independently a hydrogen atom, a halogen atom, a cyano group, a C1-C4 alkyl group, a C2-C4 alkenyl group, a C3-C6 cycloalkyl group, a C3-C6 cycloalkenyl group, an aryl group, or an aralkyl group, where the alkyl group, the C2-C4 alkenyl group, the C3-C6 cycloalkyl group, the C3-C6 cycloalkenyl group, the aryl group, and the aralkyl group optionally contain at least one atom selected from the group consisting of a halogen atom, a nitrogen atom, an oxygen atom, a sulfur atom and a silicon atom; and n is an integer of two or more.

Preferred among the foregoing phenanthrenequinone compounds (1) is a phenanthrenequinone compound in which $R_1$ and $R_2$ are independently a hydrogen atom, a halogen atom, a cyano group, or a C1-C4 alkyl group; and n is an integer of two to four (hereinafter referred to as a "phenanthrenequinone compound (1a)").

More preferred among the foregoing phenanthrenequinone compounds (1) is a phenanthrenequinone compound in which $R_1$ and $R_2$ are a hydrogen atom, and n is an integer of two to four (hereinafter referred to as a "phenanthrenequinone compound (1b)").

The present invention provides an electrode active material including at least one selected from the phenanthrenequinone compounds (1).

It is preferable to use the electrode active material of the present invention as a positive electrode active material.

The present invention provides a power storage device including a positive electrode, a negative electrode, and an electrolyte, and converting an electron transfer associated with a redox reaction into an electric energy, wherein
at least one selected from the positive electrode and the negative electrode includes the electrode active material of the present invention.

Further, the present invention provides a phenanthrene compound represented by the following general formula (2) (hereinafter referred to as a "phenanthrene compound (2)").

[Chemical formula 3]

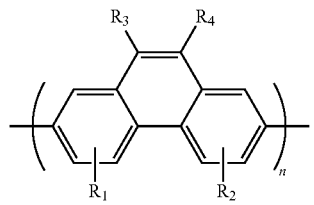

(2)

In the formula, $R_1$, $R_2$ and n are as defined above; $R_3$ and $R_4$ are a group —OX, where X is a hydrogen atom, an univalent organic group, an univalent organic metal group, or an univalent metal atom, or alternatively, are bound together to form a group —O—Y—O, where Y is a bivalent organic group, a bivalent organic metal group, or a bivalent metal atom.

Preferred among the foregoing phenanthrene compounds (2) is a phenanthrene compound in which $R_1$ and $R_2$ are independently a hydrogen atom, a halogen atom, a cyano group, or a C1-C4 alkyl group; and n is an integer of two to four (hereinafter referred to as a "phenanthrene compound (2a)").

More preferred among the foregoing phenanthrene compounds (2) is a phenanthrene compound represented by the following general formula (3) (hereinafter referred to as a "phenanthrene compound (3)").

[Chemical formula 4]

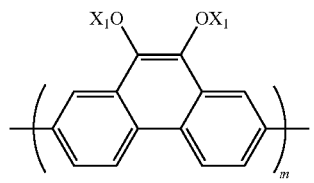

(3)

In the formula, $X_1$ is a protecting group or an alkali metal; and m is an integer of two to four. The protecting group is preferably a trialkylsilyl group or a quaternary ammonium group.

The present invention provides an organic light-emitting device including at least one selected from the foregoing phenanthrene compounds (2).

Effects of the Invention

The phenanthrenequinone compound of the present invention, when reacting with a mobile carrier, can cause a reversible redox reaction which is two-electron reaction peculiar to quinone compounds. The phenanthrenequinone compound of the present invention is insoluble in an organic solvent and is an organic compound lighter in weight than inorganic oxides used as the conventional electrode active material. As such, this phenanthrenequinone compound can be used as an electrode active material for electric power storage devices and the like, and therefore, a power storage device having a high energy density can be provided. In addition, since the redox reaction is allowed to proceed in a reversible manner even in a system using lithium ions as a mobile carrier, a power storage device having a 3 V-class high voltage can be provided.

Therefore, according to the present invention, it is possible to provide a power storage device having a high output and high capacity, and being excellent in cycle characteristics and capable of being utilized in reducing the weight and size and improving the functionality of portable electronic equipment. In addition, since a phenanthrene compound serving as a precursor of the phenanthrenequinone compound has a fluorescence property, a novel organic light-emitting device can be provided.

BEST MODE FOR CARRYING OUT THE INVENTION

Phenanthrenequinone Compounds

Figure 1:
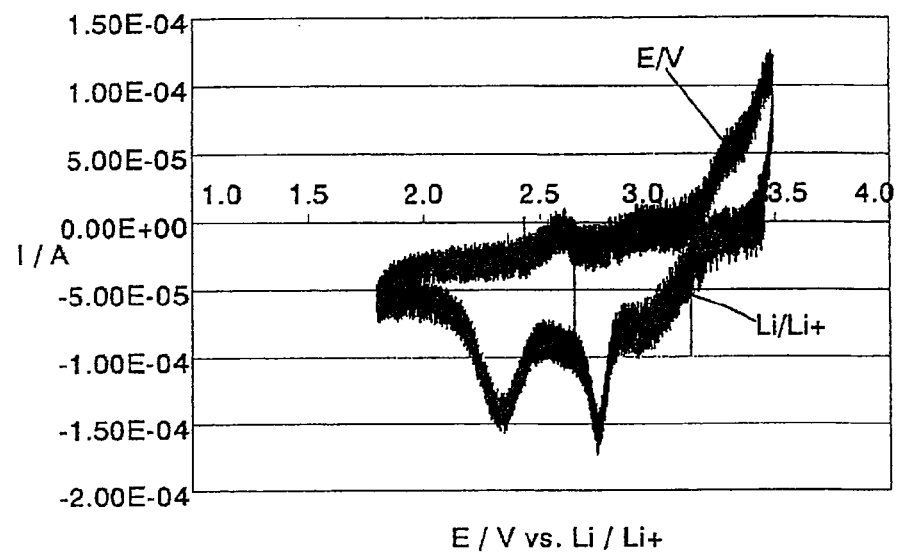
FIG. 1 is a cyclic voltammogram of a battery system for evaluation fabricated in Test Example 1.

Each of the groups represented by symbols $R_1$ to $R_7$, X, $X_1$, $X_2$ and Y in the general formulae herein is specifically as follows.

The protecting group is not particularly limited as long as it is a cation group, examples of which include trialkylsilyl having three C1-C4 straight or branched chain alkyl substituents such as tert-butyldimethylsilyl and tert-butyldiethylsilyl; arylsilyl having a total of three substituents therein selected from a C1-C4 straight or branched chain alkyl group and an aryl group, such as tert-butyldiphenylsilyl; a quaternary ammonium group, such as alkyl tetraethylammonium, and 3-ethyl methyl imidazolinium; and the like. Examples of the univalent metal atom include an alkali metal, such as potassium, sodium, and lithium, and the like. Examples of the bivalent metal atom include an alkaline earth metal, such as calcium, strontium, barium, and magnesium, and the like.

Examples of the halogen atom include fluorine, chlorine, bromine, iodine, and the like. Examples of the C1-C4 alkyl group include a C1-C4 straight or branched chain alkyl group, such as methyl, ethyl, n-propyl, iso-propyl, n-butyl, iso-butyl, and tert-butyl. Example of the C2-C4 alkenyl group include a C2-C4 straight or branched chain alkenyl group, such as vinyl, 1-propenyl, 2-propenyl, 1-methyl-1-propenyl, 2-methyl-1-propenyl, 2-methyl-2-propenyl, 2-propenyl, 2-butenyl, 1-butenyl, and 3-butenyl.

Examples of the C3-C6 cycloalkyl group include cyclopropyl, cyclobutyl, cyclopentyl, cyclohexyl, and the like. Examples of the C3-C6 cycloalkenyl group include cyclopropenyl, cyclobutenyl, cyclopentenyl, cyclohexenyl, methyl cyclopentenyl, and the like.

The aryl group may be an aryl group optionally having at least one substituent on a phenyl ring or a naphthalene ring, the substituent being selected from the group consisting of a C1-C4 straight or branched chain alkyl group, a C1-C4 straight or branched chain alkoxy group, a nitro group, and a halogen atom. Examples of such an aryl group include phenyl, methylphenyl, nitrophenyl, methoxyphenyl, chlorophenyl, biphenyl, α-naphthyl, β-naphthyl, and the like.

The aralkyl group (aryl-alkyl group) may be an aralkyl group in which one to three aryl groups are substituted in a C1-C4 straight or branched chain alkyl group. Example of such an aralkyl group include benzil, methylbenzyl, nitrobenzyl, methoxybenzyl, chlorobenzyl, phenylethyl, 1-methyl-1-phenylethyl, 1,1-dimethyl-2-phenylethyl, 1,1-dimethyl-3-phenylpropyl, α-naphthylmethyl, β-naphthylmethyl, and the like.

The phenanthrenequinone compound (1) of the present invention is a novel compound that has not been previously reported. In the phenanthrenequinone compound (1), the number of reaction electrons that can contribute to a redox reaction is two or approximately equal to two, that is, is equal or close to the theoretical number of reaction electrons of quinone compounds, and therefore has a high energy density. Further, the phenanthrenequinone compound (1) is extremely low in solubility or insoluble in an organic solvent. Furthermore, since the phenanthrenequinone compound (1) is an organic compound, it is light in weight as compared with, for example, inorganic oxides as used as the conventional electrode active material.

As such, the phenanthrenequinone compound (1) can be suitably used, for example, as an electrode active material for a power storage device, and can contribute to the reduction in weight and size and the improvement in the energy density of various power storage devices. Among the phenanthrenequinone compounds (1), in view of the ease of synthesis, the phenanthrenequinone compound (1a) is preferred, and the phenanthrenequinone compound (1b) is more preferred.

The phenanthrene compound (2) is an oligomer or a polymer of 9,10-phenanthrenequinone or a derivative thereof, which is also a novel compound that has been not previously reported. The phenanthrene compound (2) is useful, for example, as a synthesis intermediate of the phenanthrenequinone compound (1) and can be used as a material for an organic light-emitting device. The 9,10-phenanthrenequinone or a derivative thereof serving as a raw material of the phenanthrene compound (2) is one of orthoquinone compounds having two ketone groups at the ortho position. Among the phenanthrene compounds (2), in view of the ease of synthesis and others, the phenanthrene compound (2a) is preferred, and the phenanthrene compound (3) is more preferred.

In the present invention, by oligomerizing or polymerizing 9,10-phenanthrenequinone or a derivative thereof, the insolubility in an organic solvent can be achieved without causing a reduction in the number of reaction electrons due to the repulsion between electrons as caused in the conventional conductive polymer compound. The reason for this is considered as follows.

In using an organic compound as an electrode active material, in general, there are two problems that must be solved: the insolubilization in an organic solvent and the improvement in energy density. As a method of making an organic compound to be insoluble in an organic solvent, oligomerization or polymerization is generally used. On the other hand, the energy density (mAh/g) of an electrode active material is determined from the following equation:

Energy density=[(Number of reaction electrons×96,500)/Molecular weight]×(1,000/3,600).

Specifically, in order to improve the energy density, it is necessary to increase the number of reaction electrons and prevent the increase of the molecular weight. In the conventional conductive polymer compound such as polyaniline, although the molecular weight is increased by polymerization, the number of the reaction electrons is decreased, resulting in a reduced energy density. As such, the insolubilization in an organic solvent and the improvement in energy density are two conflicting problems.

On the other hand, in 9,10-phenanthrenequinone, conjugated electron clouds are present over the entire molecule. When 9,10-phenanthrenequinones are oligomerized or polymerized, depending on the method of bonding, the conjugated electron clouds may spread over the entire molecule of the resultant oligomer or polymer, and thus the repulsion between electrons may occur as in the conventional conductive polymer compound, which may possibly result in a decrease of the number of reaction electrons. In order to avoid such a decrease, the oligomerization or polymerization must be performed in such a manner that the conjugated electron clouds will not spread over the entire molecule, possibly by the following two methods.

One is a method in which a site having no π-electron, the n-electron that will form conjugated electron clouds, is intercalated into an organic compound having conjugated electron clouds, thereby to interrupt the spread of the conjugated electron clouds. However, the intercalation of the site having no n-electron increases the molecular weight, and the site generally has no relevance to the redox reaction. Therefore, this method is not preferable in view of the improvement in energy density. The other is a method in which chemical bonds are formed such that the organic compound has a three-dimensionally non-planar structure. Since the conjugated electron clouds spread over a plane, the conjugated electron clouds are divided three-dimensionally due to the non-planar structure. It is presumed that this method can prevent both the unnecessary increase of the molecular weight and the decrease of the number of reaction electrons at the same time.

For example, the optimum structure of a dimer of 9,10-phenanthrenequinone calculated using the density functional method and the basis function 6-31G* is a structure in which two 9,10-phenanthrenequinones are bonded together with an angle of 30 to 90° therebetween, which is regarded as a stable state. This is presumably because the electronic repulsion is more reduced when the quinone sites in the molecules of the two 9,10-phenanthrenequinones are present with a certain angle therebetween than when the quinone sites are present on the same flat plane, which makes the structure stable.

In view of the above, the present inventors have found that by bonding 9,10-phenanthrenequinones with a certain angle therebetween, both the insolubilization in an organic solvent and the improvement in the energy density can be achieved at the same time. Based on this finding, by introducing a polymerization initiating site (i.e., a functional group) such as halogen atom at either one or both of the 2- and 7-positions of 9,10-phenanthrenequinones, while a protecting group is introduced into the highly reactive quinone sites, the present inventors have succeeded in obtaining the phenanthrenequinone compound (1) of the present invention. Further, the present inventors have found that by introducing a functional group at the positions other than the 2- and 7-positions, the phenanthrenequinone compound (1) can be obtained.

[Synthesis of Phenanthrenequinone Compound (1)]

The phenanthrenequinone compound (1) of the present invention can be produced with the use of the phenanthrene compound (2) in which $R_3$ and $R_4$ are a group —$OX_2$, where $X_2$ is a protecting group, by converting the group —$OX_2$ to a hydroxyl group through deprotection, and then oxidizing the hydroxyl group. This reaction can be performed as a one-step reaction, for example, by permitting a phase transfer catalyst to act on the phenanthrene compound (2) in an organic solvent.

As the organic solvent, it is possible to preferably use an organic solvent having miscibility with water and being inert to reaction, examples of which include ethers, such as tetrahydrofuran; lower alcohols, such as methanol and ethanol; hydrocarbons, such as dimethoxyethane; nitrils, such as acetonitrile; mixed solvents of two or more of these; and the like. As for the amount of the organic solvent used, an appropriate amount for allowing the reaction to proceed smoothly may be selected, without any particular limitation, according to the amount of the phenanthrene compound (2) used, the type of the phase transfer catalyst, and the like.

As the phase transfer catalyst, it is possible to use any known phase transfer catalyst, such as tetra-n-hexyl ammonium chloride, trimethyl benzyl ammonium chloride, triethyl benzyl ammonium chloride, trimethyl phenyl ammonium chloride, tetrabutylammonium fluoride, tetrabutylammonium hydrogen sulfate, tetrabutylammonium chloride, tetrabutylammonium bromide, methyl tricapryl ammonium chloride, and tetrabutyl phosphonium bromide. The amount of the phase transfer catalyst used is not particularly limited, but is preferably 100 to 200 mol % of the amount of the phenanthrene compound (2) used, and more preferably about 200 mol %. In addition, an appropriate amount of acid such as acetic acid may be added. This reaction is allowed to proceed preferably while stirring at temperatures of about 0 to 50° C., and is completed in about 1 to 24 hours. The phenanthrenequinone compound (1) is synthesized through this reaction.

The phenanthrene compound (2) serving as a starting compound of the phenanthrenequinone compound (1) can be produced with the use of a 9,10-phenanthrenequinone derivative represented, for example, by the general formula (4):

[Chemical formula 5]

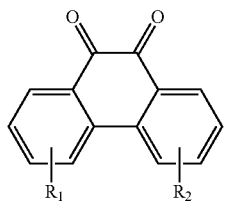

(4)

where $R_1$ and $R_2$ are the same as above (hereinafter referred to as a "9,10-phenanthrenequinone derivative (4)") as a starting compound, by the production method comprising the steps of introducing a functional group, introducing a protecting group, and multimerization.

Among the 9,10-phenanthrenequinone derivatives (4) used as a starting compound, a 9,10-phenanthrenequinone expressed as $R_1=R_2=$hydrogen atom, is preferred. Here, when either one or both of the substituent groups represented by symbols $R_1$ and $R_2$ in the 9,10-phennthrenequinone derivative (4) are a halogen atom, the step of introducing a functional group can be omitted, and the 9,10-phenanthrenequinone derivative (4) can be used as it is in the step of introducing a protecting group. A description of each step is given below.

(Step of Introducing Functional Group)

In the step of introducing a functional group, one or two halogen atom(s) that acts as a functional group for oligomerization or polymerization is introduced into the 9,10-phenanthrenequinone derivative (4). The introduction of halogen atom(s) can be achieved by a general halogenation reaction.

The halogenation is performed, for example, in the presence of a halogenating agent and, as needed, a catalyst, preferably in an organic solvent. As the halogenating agent, it is possible to use any known halogenating agent, such as chlorine, sulfuryl chloride, bromine, sulfuryl bromide, fluorine, N-fluoro pyridinium salt, and N-iodosuccinimide. As for the amount of the halogenating agent used, the amount is preferably about 1 to 3 times by mole as much as that of the 9,10-phenanthrenequinone derivative (4).

As the catalyst, it is possible to use, for example, Lewis acid, such as ferrous chloride, ferric chloride, ferrous bromide, ferric bromide, cuprous chloride, cupric chloride, cuprous bromide, cupric bromide, zinc chloride, aluminum chloride, nickel chloride, lithium chloride, tin chloride, antimony chloride, diethylaluminum chloride, dibutyltin dichloride, and triphenyltin chloride; metals, such as iron, copper, and zinc; and the like. The catalyst allows the halogenation to proceed smoothly. The amount of the catalyst used is not particularly limited, but is preferably about 0.05 to 5% by weight of the amount of the 9,10-phenanthrenequinone derivative (4) used.

Examples of the organic solvent include, for example, hydrocarbons, such as hexane, cyclohexane, and heptane; halogenated hydrocarbons, such as dichloroethane, dichloromethane, and chloroform; aromatic hydrocarbons, such as benzene, toluene, xylene, chlorobenzene, dichlorobenzene, and trichlorobenzene. When the organic solvent is used, the amount thereof is not particularly limited, but is preferably about 0.1 to 10 times by weight as much as the amount of the 9,10-phenanthrenequinone derivative (4) used. The halogenation is usually performed at temperatures of about −20 to 80° C., and preferably about −5 to 30° C.

It should be noted that in this halogenation, a specific compound can be selectively synthesized by suitably changing the halogenating agent. For example, permitting bromine to act on the 9,10-phenanthrenequinone will selectively produce 3,6-dibromo-phenantrene-9,10-dione; permitting N-iodosuccinimide to act thereon under the presence of trifluoromethane sulfonic acid will selectively produce 2,7-diiodo-phenantrene-9,10-dione; and permitting N-iodosuccinimide to act thereon under the presence of trifluoroacetic acid will selectively produce 2,7-iodo-phenantrene-9,10-dione.

(Step of Introducing Protecting Group)

In the step of introducing a protecting group, a protecting group is introduced into a 9,10-phenanthrenequinone derivative obtained in the step of introducing a functional group and represented by the general formula (5):

[Chemical formula 6]

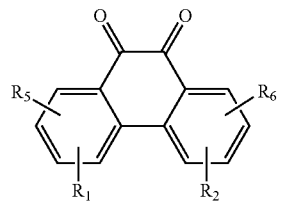

(5)

where $R_1$ and $R_2$ are the same as above; and $R_5$ and $R_6$ are independently a halogen atom or a hydrogen atom, provided that $R_5$ and $R_6$ are not simultaneously a hydrogen atom (hereinafter referred to as a "functional group-introduced compound (5)").

Examples of the functional group-introduced compound (5) include the following compounds (5a) to (5f). Among these, the compounds (5a) to (5d) are used for synthesis of a dimer, and the compounds (5e) to (5f) are used for synthesis of an oligomer or polymer higher than a dimer.

[Chemical formula 7]

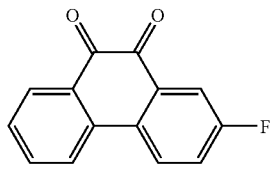
(5a)

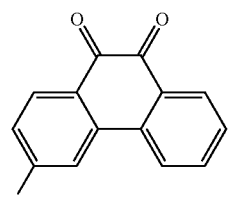
(5b)

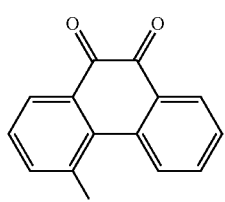
(5c)

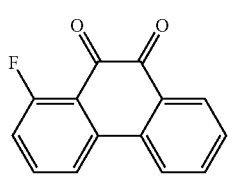
(5d)

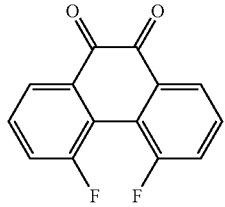
(5e)

[Chemical formula 8]

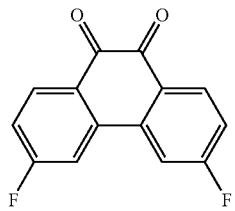
(5f)

The introduction of a protecting group into the functional group-introduced compound (5) can be performed by a known method. For example, it can be performed by allowing the functional group-introduced compound (5) to react with a silane compound or a quaternary ammonium compound in the presence of a metal catalyst and a complexing agent, preferably in an organic solvent. Examples of the silane compound include t-butyldimethylsilyl chloride, tert-butyldieth- ylsilyl chloride, t-butyldiphenylsilyl chloride, triphenylmethyl chloride, trimethylsilyl chloride, N-trimethylsilyl acetamide, N-trimethylsilyl diethylamine, N-trimethylsilyl imidazole, and the like.

Examples of the quaternary ammonium compound include tetraethylammonium chloride, 3-ethylmethyl imidazolinium chloride, and the like. Examples of the metal catalyst include zinc, and the like. Examples of the complexing agent include N,N,N',N'-tetramethylethylenediamine, and the like. Examples of the solvent include hydrocarbons such as hexane, and the like. The reaction for introducing a protecting group is preferably performed at temperatures of about 0 to 80° C.

Alternatively, any protecting group can be introduced by permitting a reducing agent such as sodium hydrosulfite to act on the functional group-introduced compound (5) in the presence of a base and an organic halogenated compound, while heating at a temperature of 80° C., preferably in an organic solvent. Examples of the base include sodium hydroxide, potassium carbonate, and the like. Examples of the organic halogenated compound include benzyl bromide, n-bromohexane, and the like.

Through these reactions, a 9,10-phenanthrene derivative represented by the general formula (6):

[Chemical formula 9]

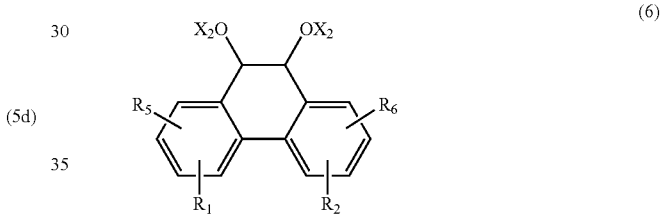
(6)

where $R_1$, $R_2$, $R_5$, $R_6$, and $X_2$ are the same as above (hereinafter referred to as a "protecting group-introduced compound (6)") can be formed.

The protecting group-introduced compound (6) is allowed to react with an alkali metal, so that the protecting group in the protecting group-introduced compound (6) is substituted by the alkali metal, whereby an alkali metal-introduced compound is formed. For this reaction, it is possible to utilize a known method for substituting the protecting group by an alkali metal, examples of which include halogen-lithium exchange reaction, and the like. According to the halogen-lithium exchange reaction, for example, by allowing the protecting group-introduced compound (6) to react with an alkyllithium reactant under anhydrous conditions and, as needed, in an organic solvent, the alkali metal-introduced compound can be obtained. Examples of the alkyllithium reactant include n-butyllithium, tert-butyllithium, and the like. The organic solvent is not particularly limited as long as it is inert to the reaction, and is exemplified by diethyl ether, tetrahydropyran, and the like. Preferably, the organic solvent is dehydrated as much as possible. This reaction is preferably allowed to proceed at temperatures of about −78° C. to room temperature.

(Step of Multimerization)

In the step of multimerization, the protecting group-introduced compound (6) or the alkali metal-introduced compound obtained in the step of introducing a protecting group is oligomerized or polymerized. Oligomerization is performed, for example, with the use of the protecting group-introduced compound (6) or the alkali metal-introduced compound as a starting compound, in the presence of an urethdione catalyst, a nickel salt, and a reducing metal, and in the absence of a solvent or in a solvent.

As the urethdione catalyst, it is possible to use any known urethdione catalyst, examples of which include trivalent phosphorus compounds, such as tris(dimethylamino)phosphine, tris(diethylamino)phosphine, triethylphosphine, tri-n-propylphosphine, triisopropylphosphine, tri-n-butylphosphine, triisobutylphosphine, tri-tert-butylphosphine, tri-n-hexylphosphine, tricyclohexylphosphine, tris(dicyclohexyl) phosphine, tri-n-octylphosphine, triphenylphosphine, tribenzylphosphine, and benzyldimethylphosphine; Lewis acid, such as boron trifluoride, and zinc trichloride; and the like. The amount of the urethdione catalyst used is not particularly limited, but is preferably 0.01 to 10% by weight of the amount of the starting compound used, and more preferably 0.1 to 2% by weight.

As the nickel salt, it is possible to use nickel chloride, nickel bromide, nickel acetate, nickel acetylacetonato, (triphenylphosphine)nickel(II) dichloride, and the like. The amount of the nickel salt used is not particularly limited, but is preferably 0.001 to 2 times by mole as much as that of the starting compound, and more preferably 0.02 to 0.1 times by mole.

Examples of the reducing metal include zinc, magnesium, aluminum, manganese, and the like. Among these, zinc is preferred. The amount of the reducing metal used is not particularly limited, but is preferably 0.1 to 4 times by mole as much as that of the starting compound, and more preferably 1 to 2 times by mole. Alternatively, a reducing agent such as sodium hydride and aluminum hydroxide may be used. It is preferable to wash these before use with a dehydrated organic solvent.

The organic solvent is not particularly limited as long as it is inert to the reaction, and is exemplified by hydrocarbons, such as hexane; aromatic hydrocarbons, such as toluene; N,N-dimethylacetamide; N,N-dimethylformamide; N-methyl-2-pyrrolidone; 1,3-dimethyl-2-imidazolidinone; a mixed solvent of two or more of these; and the like. Here, if a solvent other than aprotic solvents is used, it is preferable that the solvent is dehydrated as much as possible.

The oligomerization reaction is allowed to proceed, for example, at temperatures of about 0 to 50° C. Through this reaction, an oligomer (dimer) of the phenanthrene compound (2) of the present invention in which n is 2 is formed.

An oligomer (trimer) of the phenanthrene compound (2) of the present invention in which n is 3 is formed by, for example, allowing the functional group-introduced compound (5a) having one functional group introduced therein to react with a dioxaborolane compound represented by the general formula (7):

[Chemical formula 10]

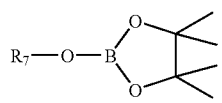

(7)

where $R_7$ is a C1-C4 alkyl group (herein after referred to as a "dioxaborolane compound (7)"), so that that the functional group in the functional group-introduced compound (5a) is substituted by a 4,4,5,5-tetramethyl-1,3,2-dioxaborolane group; and then allowing the resultant compound to further react with the functional group-introduced compound (5b) having two functional groups introduced therein.

The reaction between the dioxaborolane compound (7) and the functional group-introduced compound (5a) is allowed to proceed, for example, in the presence of an alkyllithium reactant, in an organic solvent. Although there is no particular limitation on the ratio of the dioxaborolane compound (7) to the functional group-introduced compound (5a), normally, about 1 to 1.2 moles of the dioxaborolane compound (7) is used per 1 mole of the functional group-introduced compound (5a). Examples of the alkyllithium reactant include n-butyllithium, tert-butyllithium, and the like. The organic solvent is not particularly limited as long as it is inert to the reaction, and is exemplified by diethyl ether, tetrahydropyran, and the like. Preferably, the organic solvent is dehydrated as much as possible. This reaction is preferably performed at temperatures of about −78° C. to room temperature and is completed in about 1 to 5 hours.

The reaction between a compound in which the functional group in the functional group-introduced compound (5a) is substituted by a 4,4,5,5-tetramethyl-1,3,2-dioxaborolane group (hereinafter referred to as a "dioxaborolane group-introduced compound") and the functional group-introduced compound (5b) is allowed to proceed, for example, in the presence of a palladium catalyst and a base, preferably in a solvent. Although there is no particular limitation on the ratio between the two compounds, normally, about 1 to 1.2 moles of the dioxaborolane group-introduced compound is used per 1 mole of the functional group-introduced compound (5b).

Examples of the palladium catalyst include triphenylphosphine palladium, bis(triphenylphosphine) palladium, tetrakis(triphenylphosphine) palladium, bis(trialkylphosphine) palladium, palladium acetate, and the like. Among these, complexes of phosphines and palladium are preferred. As the base, it is possible to use any known base, such as sodium hydroxide, potassium hydroxide, sodium carbonate, potassium carbonate, cesium carbonate, and sodium hydride. As for the amounts of the palladium catalyst and the base used, appropriate amounts may be selected according to the amounts of the two compounds to be subjected to the reaction.

As for the solvent, a solvent inert to the reaction may be selectively used. Examples of such a solvent include aromatic hydrocarbons, such as toluene and xylene; water; mixed solvents of two or more of these; and the like. This reaction is allowed to proceed at temperatures of about 0 to 80° C. and is completed in about 1 to 24 hours.

An oligomer of the phenanthrene compound (2) in which n=4 is formed by, for example, introducing two functional groups into the dimer and allowing the resultant compound to react with the dioxaborolane group-introduced compound in the same manner as described above. A polymer in which n=5 or more is formed in the same manner.

The reaction in each step is preferably allowed to proceed in an inert atmosphere such as an argon atmosphere or in a non-oxidizing atmosphere. The intended material to be obtained in each step can be easily isolated from a finally-obtained reaction mixture by performing some general isolation/refinement means in combination, such as filtration, centrifugal separation, extraction, chromatography, concentration, recrystallization, and washing.

[Electrode Active Material and Power Storage Device]

The phenanthrenequinone compound (1) of the present invention can be used as a positive electrode active material and a negative electrode active material. In fabricating a power storage device including the phenanthrenequinone compound (1) of the present invention, the compound (1) is used for at least one of the positive electrode and the negative electrode, or alternatively used for both of the positive electrode and the negative electrode. In the case of using for either the positive electrode or the negative electrode, the active material used for the other electrode may be any active material widely used as an active material for a power storage device.

The power storage device of the present invention includes a positive electrode, a negative electrode, a separator, and an electrolyte. The positive electrode and the negative electrode are arranged so as to face each other with the separator interposed therebetween.

The positive electrode includes a positive electrode current collector and a positive electrode active material layer, which are arranged such that the positive electrode active material layer is in the separator side. As the positive electrode current collector, it is possible to use any material widely used in this field, which is exemplified by a porous or non-porous material in the form of sheet or film made of a metal such as nickel, aluminum, gold, silver, copper, stainless steel, and an aluminum alloy. The sheet or film is specifically a metal foil, a mesh material, and the like. Further, a carbonaceous material such as carbon may be applied onto a surface of the positive electrode current collector for the purpose of reducing the resistance, imparting the catalyst effect, strengthening the bond between the positive electrode active material layer and the positive electrode current collector by bonding them chemically or physically, and other purposes.

The positive electrode active material layer is provided on at least one surface of the positive electrode current collector, and includes a positive electrode active material and, as needed, an additional material such as a conductive agent, an ion conductive agent, and a binder. When the phenanthrenequinone compound (1) is used as the positive electrode active material, it is possible to preferably use as the negative electrode active material, for example, a carbon compound such as carbon, graphitized carbon (graphite), amorphous carbon; lithium metal, a lithium-containing composite nitride, a lithium-containing titanium oxide, Si, a Si oxide, Sn, and the like. Alternatively, it is possible to use activated carbon as a counter electrode, thereby to form a capacitor. It should be noted that, preferably, the phenanthrenequinone compound (1) is used as the positive electrode active material.

The conductive agent and the ion conductive agent are used, for example, for the purpose of reducing the resistance of the electrode. As the conductive agent, it is possible to use any material widely used in this field, which is exemplified by a carbon material, such as carbon black, graphite, and acetylene black; a conductive polymer compound, such as polyaniline, polypyrrole, and polythiophene; and the like. As the ion conductive agent, it is also possible to use any material widely used in this field, which is exemplified by a solid electrolyte, such as polyethylene oxide; a gelled electrolyte, such as polymethyl methacrylate, and polymethyl methacrylate, and the like.

The binder is used, for example, for the purpose of improving the bonding ability between components of the electrode. As the binder, it is also possible to use any material widely used in this field, which is exemplified by polyvinylidene fluoride, vinylidene fluoride-hexafluoropropylene copolymer, vinylidene fluoride-tetrafluoroethylene copolymer, polytetrafluoroethylene, styrene-butadiene copolymer rubber, polypropylene, polyethylene, polyimide, and the like.

The negative electrode includes a negative electrode current collector and a negative electrode active material layer, which are arranged such that the negative electrode active material layer is in the separator side. As the negative electrode current collector, it is possible to use a porous or non-porous material in the form of sheet or film made of the same metal as used in the positive electrode current collector, which is specifically exemplified by a metal foil, a mesh material, and the like. Further, as in the case of the positive electrode current collector, a carbon material such as carbon may be applied onto a surface of the negative electrode current collector for the purpose of reducing the resistance, imparting the catalyst effect, strengthening the bond between the negative electrode active material layer and the negative electrode current collector, and other purposes.

The negative electrode active material layer is provided on at least one surface of the negative electrode current collector, and includes a negative electrode active material and, as needed, additional materials such as a conductive agent, an ion conductive agent, and a binder. When the phenanthrenequinone compound (1) is used as the negative electrode active material, it is possible to preferably use as the positive electrode, for example, a lithium-containing metal oxide, such as $LiCoO_2$, $LiNiO_2$, and $LiMn_2O_4$; and the like. The conductive agent, ion conductive agent, and binder included in the negative electrode active material layer may be the same conductive agent, ion conductive agent, and binder as included in the positive electrode active material layer.

The separator is provided between the positive electrode and the negative electrode. As the separator, for example, a sheet or film material having a predetermined degree of ion permeability, as well as mechanical strength, insulating property, and the like may be used. Examples of the separator include a porous material in the form of sheet or film, such as a microporous film, a woven fabric, and a non-woven fabric. The separator may be made of various resin materials, but in view of the durability, the shut-down function, the safety of a battery, and others, is preferably made of polyolefin such as polyethylene and polypropylene. Here, the shutdown function is a function that works when the battery temperature is abnormally elevated in such a way that the throughpores are closed to interrupt the migration of ions, thereby to shut down the battery reaction.

As the electrolyte, it is possible to use, for example, a liquid electrolyte, a solid electrolyte, a gelled electrolyte, and the like. Among these, a gelled electrolyte is preferred.

The liquid electrolyte includes a supporting salt and, as needed, an organic solvent. As the supporting salt, any supporting salt used in lithium ion batteries and non-aqueous electric double layer capacitors may be used. Specifically, a supporting salt containing a cation and an anion as listed below may be used.

Examples of the cation includes a cation of an alkali metal, such as lithium, sodium, and potassium; a cation of an alkaline earth metal, such as magnesium; and a cation of quaternary ammonium, such as tetraethylammonium and 1,3-ethylmethyl imidazolium. These cations may be used alone or in combination of two or more.

Examples of the anion includes halide anion, perchlorate anion, trifluoromethanesulfonate anion, tetrafluoroborate anion, trifluorohexafluorophosphate anion, trifluoromethanesulfonate anion, bis(trifluoromethanesulfonyl)imide anion, bis(perfluoroethylsulfonyl)imide anion, and the like. These anions may be used alone or in combination of two or more.

When the supporting salt itself is in a liquid state, the supporting salt may be mixed or may not be mixed with the organic solvent. When the supporting salt is in a solid state, the supporting salt is preferably dissolved in the organic solvent. As the organic solvent, any organic solvent used in lithium ion batteries and non-aqueous electric double layer capacitors may be used. Among these, non-aqueous solvents, such as ethylene carbonate, propylene carbonate, dimethyl carbonate, diethyl carbonate, methylethyl carbonate, γ-butyrolactone, tetrahydrofuran, dioxolane, sulfolane, dimethylformamide, and acetonitrile may be preferably used. These organic solvents may be used alone or in combination of two or more.

The solid electrolyte is exemplified by $Li_2S$—$SiS_2$-lithium compound, where the lithium compound is at least one selected from the group consisting of $Li_3PO_4$, LiI, and $Li_4SiO_4$; $Li_2S$—$P_2O_5$; $Li_2S$—$B_2S_5$; $Li_2S$—$P_2S_5$—$GeS_2$; sodium/alumina ($Al_2O_3$); an amorphous polyether having a low phase-transition temperature (Tg); an amorphous vinylidene fluoride copolymer; and a blend of different polymers; polyethylene oxide; and the like.

The gelled electrolyte is exemplified by a gelled electrolyte including a resin material, an organic solvent, and a supporting salt. Examples of the resin material include polyacrylonitrile, a copolymer of ethylene and acrylonitrile, a cross-linked polymer of these, and the like. A preferable example of the organic solvent is a non-aqueous solvent having a low-molecular weight, such as ethylene carbonate and propylene carbonate. Examples of the supporting salt are the same as listed above. As for the power storage device of the present invention, specific examples thereof include a primary battery, a secondary battery, a capacitor, an electrolytic condenser, a sensor, an electrochromic device, and the like.

EXAMPLES

The present invention is specifically described below with reference to examples and test examples.

Example 1

(1) Synthesis of 2-iodo-phenantrene-9,10-dione

Into a 200 mL volume eggplant-shaped flask, 10.0 g of 9,10-phenanthrenequinone, 54.8 g of trifluoroacetic acid, and 21.6 g of N-iodosuccinimide were added at room temperature, heated to 35° C., and then stirred for 36 hours in an argon atmosphere. The reaction mixture was poured into icy water. The solid precipitate was collected by filtration and recrystallized with tetrahydrofuran, thereby to give 12.1 g of 2-iodo-phenantrene-9,10-dione (yield 75%) as an orange-colored solid.

(2) Synthesis of 9,10-bis(t-butyldimethylsilyloxy)-2-iodo-9,10-dihydro-phenanthrene Into a 200 mL volume eggplant-shaped flask, 1.0 g of 2-iodo-phenantrene-9,10-dione, 3.0 g of zinc powder, 100 mL of dichloromethane, 1.8 g of N,N,N',N'-tetramethylethylenediamine, and 1.9 g of t-butyl dimethyl chlorosilane (hereinafter "TBDMSCL") were added and stirred at room temperature over night in an argon atmosphere. The reaction mixture was further mixed with 1.0 g of TBDMSCL, and stirred for 5 hours. The resultant reaction mixture was concentrated and subjected to column purification (filler: granules of neutral silica gel, solvent: hexane), and recrystallized with hexane, thereby to give 1.19 g of 9,10-bis(t-butyldimethylsilyloxy)-2-iodo-9,10-dihydro-phenanthrene (yield 80%) as a white-colored solid.

(3) Synthesis of 9,10-bis(t-butyldimethylsilyloxy)-2-iodo-9,10-dihydro-phenanthrene dimer To 3 mL of dehydrated toluene, 250 mg of the above-prepared 9,10-bis(t-butyldimethylsilyloxy)-2-iodo-9,10-dihydro-phenanthrene, 150 mg of bis(triphenylphosphine)nickel(II) dichloride, 120 mg of triphenylphosphine, 149 mg of sodium hydride washed with dehydrated hexane, and 90 mg of zinc powder were added and stirred at 80° C. for 8 hours in an argon atmosphere. The resultant reaction mixture was subjected to column purification (filler: granules of neutral silica gel, solvent: hexane and hexane/ethyl acetate=10:1) and acetone washing, and the white-colored deposit was collected by filtration, thereby to give 100 mg of 9,10-bis(t-butyldimethylsilyloxy)-2-iodo-9,10-dihydro-phenanthrene dimer (yield 50%) as a white-colored solid.

In the $^1$H-NMR spectrum of the compound thus obtained, there appeared a peak at 0.16 ppm, the peak being attributed to hydrogen (24 protons) on the methyl group in the t-butyldimethylsilyl group. Further, there appeared peaks at 1.12 ppm and 1.21 ppm, the peaks being attributed to hydrogen (18 protons each) on the t-butyl group in the t-butyldimethylsilyl group. Furthermore, there appeared peaks at 7.56 to 7.64 ppm (4 protons), 8.02 ppm (2 protons), 8.22 to 8.28 ppm (2 protons), 8.63 ppm (2 protons), 8.64 to 8.69 ppm (2 protons) and 8.73 ppm (2 protons), the peaks being attributed to hydrogen (14 protons in total) on the aromatic ring. From this result, the above-titled compound was identified.

(4) Deprotection Reaction

Into a 20 mL volume eggplant-shaped flask, 80 mg of the above-prepared 9,10-bis(t-butyldimethylsilyloxy)-2-iodo-9,10-dihydro-phenanthrene dimer, 10 mL of tetrahydrofuran, 43 mg of ethanol, and 0.4 mL of tetrabutylammonium fluoride were added and stirred at room temperature in air. The resultant reaction mixture was allowed to stand. Thereafter, the precipitate was collected by filtration and washed, thereby to give 28 mg of a phenanthrenequinone compound represented by the following chemical structural formula (1b-1) (hereinafter referred to as a "phenanthrenequinone compound (1b-1)") (yield 76%) as a reddish brown-colored solid.

[Chemical formula 11]

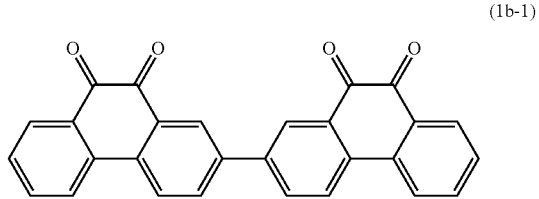

(1b-1)

In the IR spectrum of the phenanthrenequinone compound (1b-1), there appeared a peak at 1674 $cm^{-1}$, the peak presumably being attributed to the stretching vibration of the carbonyl group in a quinone compound. Further, there appeared a new peak at 1593 $cm^{-1}$, the peak not being observed in the spectrum of 9,10-bis(t-butyldimethylsilyloxy)-2-iodo-9,10-dihydro-phenanthrene dimer. From this result, the above-titled compound was identified.

Example 2

(1) Synthesis of 9,10-bis(t-butyldimethylsilyloxy)-2-(4,4,5,5-tetramethyl-1,3,2-dioxaborolan-2-yl)-9,10-dihydrophenanthrenequinone Into a 100 mL volume eggplant-shaped flask, 6.4 g of 9,10-bis(t-butyldimethylsilyloxy)-2-iode-9,10-dihydrophenanthrenequinone and 50 mL of dehydrated diethyl ether were added and cooled to −78° C. To the cooled solution, 9.5 mL of t-butyllithium (a 1.31 mol n-pentane solution) was added dropwise, and further stirred for 1 hour. To the resultant mixture, 2.6 mL of 2-isopropoxy-4,4,5,5-tetramethyl-1,3,2-dioxaborolane, and heated gradually to room temperature while being stirred. The resultant reaction mixture was subjected to column purification (filler: granules of neutral silica gel, solvent: hexane/ethyl acetate=10:1), and then concentrated, thereby to give 4.2 g of 9,10-bis(t-butyldimethylsilyloxy)-2-(4,4,5,5-tetramethyl-1,3,2-dioxaborolan-2-yl)-9,10-dihydrophenanthrenequinone (yield 65%) represented by the following chemical structural formula, as a white-colored solid.

[Chemical formula 12]

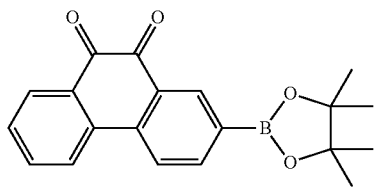

(2) Synthesis of 9,10-bis(t-butyldimethylsilyloxy)-9,10-dihydrophenanthrenequinone trimer Into a 20 mL volume Schlenk flask, 347 mg of 9,10-bis(t-butyldimethylsilyloxy)-2,7-diiodo-9,10-dihydrophenanthrenequinone, 682 mg of 9,10-bis(t-butyldimethylsilyloxy)-2-(4,4,5,5-tetramethyl-1,3,2-dioxaborolan-2-yl)-9,10-dihydrophenanthrenequinone, 60 mg of bis[tri(t-butyl)phosphine]palladium, 1.0 g of cesium carbonate, 48 μL of water, and 5 mL of degassed toluene were added and stirred at 60° C. over nigh. The resultant reaction mixture was subjected to column purification (filler: granules of neutral silica gel, solvent: ethyl acetate), and further subjected to purification by gel permeation chromatography, thereby to give mg of 9,10-bis(t-butyldimethylsilyloxy)-9,10-dihydrophenanthrenequinone trimer (yield 48%) represented by the following chemical structural formula (3a), as a white-colored solid. In the chemical structural formula (3a), the "group-OTBS" represents a t-butyldimethylsilyloxy group.

[Chemical formula 13]

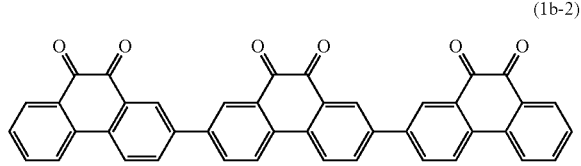

(3a)

The $^1$H NMR and $^{13}$C NMR of the resultant 9,10-bis(t-butyldimethylsilyloxy)-9,10-dihydrophenanthrenequinone trimer revealed that:

$^1$H-NMR (400 MHz, CDCl$_3$) δ: 0.17 (s, 36H), 1.20 (s, 18H), 1.22 (s, 36H), 7.56 to 7.64 (m, 4H), 8.03 (dd, J=4.0, 2.0 Hz, 2H), 8.05 (dd, J=4.0, 2.0 Hz, 2H), 8.22 to 8.26 (m, 2H), 8.64 (d, J=2.0 Hz, 4H), 8.65 to 8.70 (m, 2H), 8.74 (d, J=8.8 Hz, 2H), and 8.78 (d, J=8.8 Hz, 2H); and $^{13}$C-NMR (100 MHz, CDCl$_3$) δ: 3.2, 3.1, 18.9, 19.0, 26.7, 26.8, 121.4, 121.5, 122.3, 123.00, 123.03, 123.1, 124.0, 124.2, 124.9, 125.9, 126.6, 126.7, 127.5, 130.2, 130.65, 130.69, 137.5, 137.7, 137.9, 138.51, and 138.53.

In the $^1$H-NMR spectrum of the resultant compound, there appeared a peak at 0.17 ppm, the peak being attributed to the hydrogen (36 protons) on the methyl group in the t-butyldimethylsilyl group. Further, there appeared peaks at 1.20 ppm and 1.22 ppm, the peaks being attributed to hydrogen (54 protons) on the t-butyl group in the t-butyldimethylsilyl group. Furthermore, there appeared peaks at 7.56 to 7.64 ppm (4 protons), 8.03 ppm (2 protons), 8.05 ppm (2 protons), 8.22 to 8.26 ppm (2 protons), 8.64 ppm (4 protons), 8.65 to 8.70 ppm (2 protons), 8.74 ppm (2 protons), 8.78 ppm (2 protons), the peaks each being attributed to hydrogen (20 protons in total) on the aromatic ring. From this result, the above-titled compound was identified.

(3) Deprotection Reaction

In a 20 mL volume glass container, 187 mg of the above-prepared 9,10-bis(t-butyldimethylsilyloxy)-9,10-dihydrophenanthrenequinone trimer, 20 mL of tetrahydrofuran, 64 μL of acetic acid, and 2.3 mL of tetrabutylammonium fluoride were placed and stirred at room temperature in air. The resultant reaction mixture was allowed to stand. Thereafter, the precipitate was collected by filtration and washed, thereby to give 87 mg of a phenanthrenequinone compound represented by the following chemical structural formula (1b-2) (hereinafter referred to as a "phenanthrenequinone compound (1b-2)") (yield 75%), as a reddish brown-colored solid.

[Chemical formula 14]

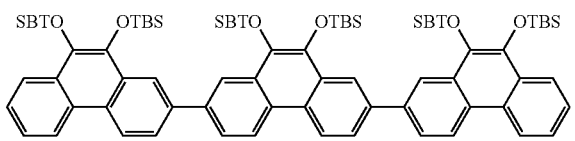

(1b-2)

In the IR spectrum of the above phenanthrenequinone compound (1b-2), there appeared a peak at 1674 cm$^{-1}$, the peak presumably being attributed to the stretching vibration of the carbonyl group in a quinone compound. Further, there appeared a peak at 1593 cm$^{-1}$, the peak presumably being attributed to the antisymmetrical expansion and contraction of the conjugate C=C—C=C in a quinone compound. Furthermore, there appeared a peak at 1285 cm$^{-1}$, the peak presumably being attributed to a quinone compound. From this result, the above-titled compound was identified.

Test Example 1

In a dry box provided with a gas purifier, 20 mg of the phenanthrenequinone compound (1b-1) serving as an electrode active material and 20 mg of acetylene black serving as a conductive agent were uniformly mixed in an argon gas atmosphere. To the resultant mixture, 1 mL of N-methyl-2-pyrrolidone was added as a solvent, and further, 5 mg of polyvinylidene fluoride serving as a binder was added in order to bond the electrode active material and the conductive agent, followed by uniform mixing, thereby to prepare a black-colored slurry. This slurry was applied onto a 20-μm-thick aluminum foil (current collector) and dried under vacuum at room temperature for 1 hour. After drying, a 13.5 mm disc was punched out of the resultant slurry-coated aluminum foil, whereby an electrode having a thickness of 60 µm was produced.

The electrode thus obtained was used as a working electrode. By immersing the working electrode into an electrolyte together with a counter electrode and a reference electrode each made of metallic lithium, a battery system for evaluation was fabricated, and the potential sweeping was performed in a potential range from 1.0 to 3.0 V versus lithium reference. The sweeping rate was 0.1 mV/sec. The electrolyte was a mixture containing propylene carbonate and ethylene carbonate at a volume ratio of 1:1 with lithium fluoroborate added thereto at a concentration of 1.0 mol. The cyclic voltammogram thus obtained is shown in FIG. 1. The cyclic voltammogram in FIG. 1 shows the result of the potential sweeping performed with the use of the electrode containing the phenanthrenequinone compound (1b-1).

As shown in FIG. 1, at the beginning of sweeping of around 2.7 V, a current peak representing the conversion of the quinone (C=O) in the quinone sites to O—Li that occurred in association with reduction reaction was observed; and at around 2.4 V, a current peak representing the reduction reaction in the second phase was observed. This indicates that the phenanthrenequinone compound (1b-1) reacts with Li ions. Further, current peaks representing oxidation reaction were observed at around 2.6 V and around 3.0 V. This indicates that the reaction of the phenanthrenequinone compound (1b-1) is reversible. For comparison, in place of the phenanthrenequinone compound (1b-1), 1,4-benzoquinone, which is one of the para-quinone compounds, was used to produce an electrode, and a test was performed under the same conditions as above except that the electrode thus produced was used. In this case, no clear sign of redox reaction was observed.

Despite the fact that the phenanthrenequinone compound (1b-1) is a molecule having conjugated electron clouds, two clear peaks were observed as in the case of 9,10-phenanthrenequinone being a monomer molecule. The foregoing results confirmed that the phenanthrenequinone compound (1b-1) being a novel compound reversibly electrochemically reacts with lithium ions. In addition, despite the concern about a decrease of the number of reaction electrons and reduction in reaction potential as observed in the conventional conductive polymer compounds, these disadvantages were not observed in the phenanthrenequinone compound (1b-1). This indicates that if the phenanthrenequinone compound (1b-1) is in the form of a dimer, the electron conjugation is three-dimensionally interrupted. It is understood from the above results that the phenanthrenequinone compound (1) is a compound that suffers no decrease of the number of reaction electrons and no reduction in the reaction potential, is hard to dissolve in an electrolyte in a liquid state, and is useful as an electrode active material.

Test Example 2

Figure 2:
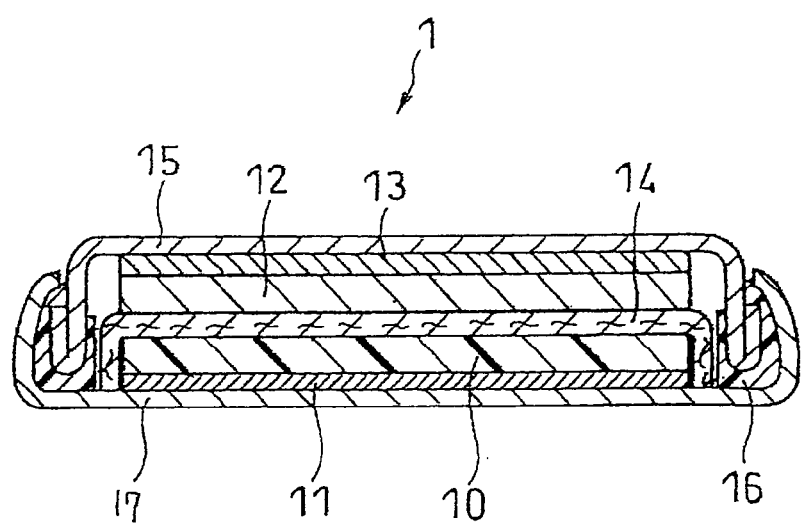
FIG. 2 is a longitudinal sectional view schematically showing the configuration of a coin battery as one embodiment of the present invention.

A coin battery 1 having a structure as shown in FIG. 2 was fabricated. FIG. 2 is a longitudinal sectional view schematically showing the configuration of the coin battery 1 as one embodiment of the present invention. The electrode produced in Text Example 1 was used a positive electrode (a laminated body of a positive electrode active material 10 and a positive electrode current collector 11). First, this positive electrode was placed in a case 17 such that the positive electrode current collector 11 is brought into contact with the inner surface of the case 17, and on the positive electrode, a separator 14 made of porous polyethylene sheet was disposed. Subsequently, a non-aqueous electrolyte was injected into the case 17. As the non-aqueous electrolyte, an electrolyte prepared by dissolving lithium fluoroborate at a concentration of 1.0 mol in a mixed solvent containing ethylene carbonate and propylene carbonate at a weight ratio of 1:1 was used.

On the other hand, a negative electrode current collector 13 and a negative electrode active material layer 12 were press-fitted in this order onto the inner surface of a sealing plate 15. As the negative electrode material layer 12, a 300-µm-thick graphite layer was used. Here, the graphite layer had preliminarily charged at a current value of 0.1 mA/cm$^2$ with the use of a Li metal counter electrode, so that lithium ions were intercalated into the graphite layer beforehand. As the negative current collector 13, a 100-µm-thick stainless steel foil was used.

The case 17 with the positive electrode disposed thereon and the sealing plate 15 with the negative electrode disposed thereon were stacked, with a gasket 16 placed therebetween around the circumference, such that the negative electrode active material layer 12 was brought into close contact with the separator 14, and subsequently crimped together with a pressing machine, whereby a coin battery of the present invention having a thickness of 16 mm and a diameter of 20 mm was produced. For comparison, an electrode was produced in the same manner as in Test Example 1 except that 1,4-benzoquinone was used in place of the phenanthrenequinone compound (1b-1), and a coin battery for comparison was produced in the same manner as described above except that the resultant electrode was used as the positive electrode.

Figure 3:
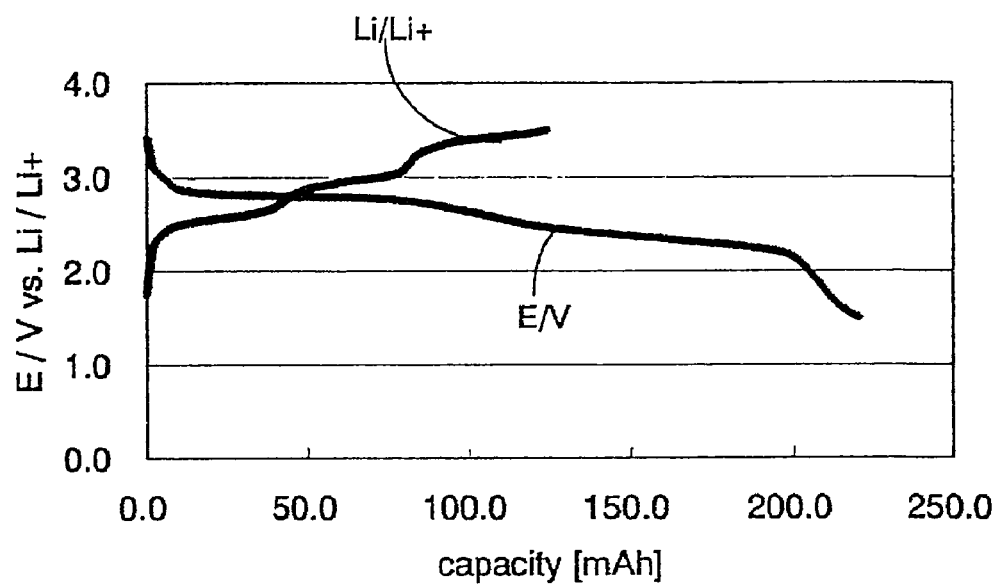
FIG. 3 is a charge-discharge curve of a coin battery fabricated in Test Example 2.

The coin batteries of the present invention and for comparison obtained in the above-described manner were subjected to constant current charge/discharge at a current of 0.133 mA in a voltage range from 2.5 V to 4.0 V, to evaluate the reaction reversibility in lithium ion systems. The results are shown in FIG. 3. FIG. 3 is a charge-discharge curve of the coin battery of the present invention. In the graph shown in FIG. 3, the vertical axis represents the battery potential (V), and the horizontal axis represents the discharge capacity (mAh). FIG. 3 confirmed that in the coin battery of the present invention, which is one of the batteries using lithium ions as a mobile carrier, reversible charge/discharge reaction proceeds. Thereafter, the charge/discharge cycle test was repeated to a total of 5 cycles, during which no significant deterioration in capacity was observed.

Test Example 3

Figure 4:
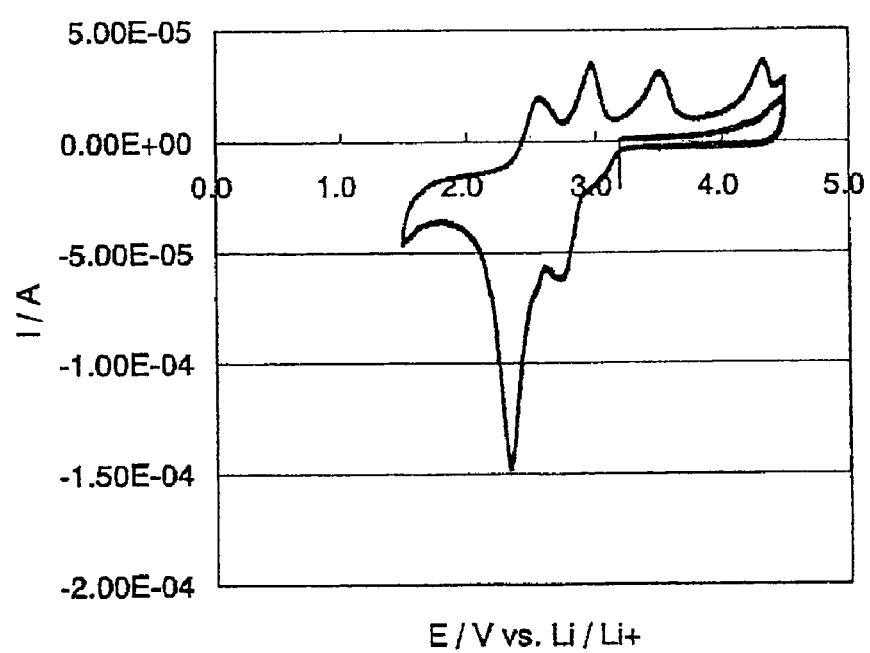
FIG. 4 is a cyclic voltammogram of a battery system for evaluation fabricated in Test Example 3.

A test was performed in the same manner as in Test Example 1 except that the phenanthrenequinone compound (1b-2) was used as the electrode active material in place of the phenanthrenequinone compound (1b-1). The cyclic voltammogram thus obtained is shown in FIG. 4. As shown in FIG. 4, at the beginning of sweeping of around 2.8 V, a peak representing the conversion of the quinone (C=O) in the quinone sites to O—Li that occurred in association with reduction reaction was observed; and at around 2.5 V, a current peak representing the reduction reaction in the second phase was observed. This indicates that the phenanthrenequinone compound (1b-2) reacts with Li ions. Further, current peaks representing oxidation reaction were observed in the region from 2.5 V to 4.3 V. This indicates that the reaction of the phenanthrenequinone compound (1b-2) is reversible.

Test Example 4

Figure 5:
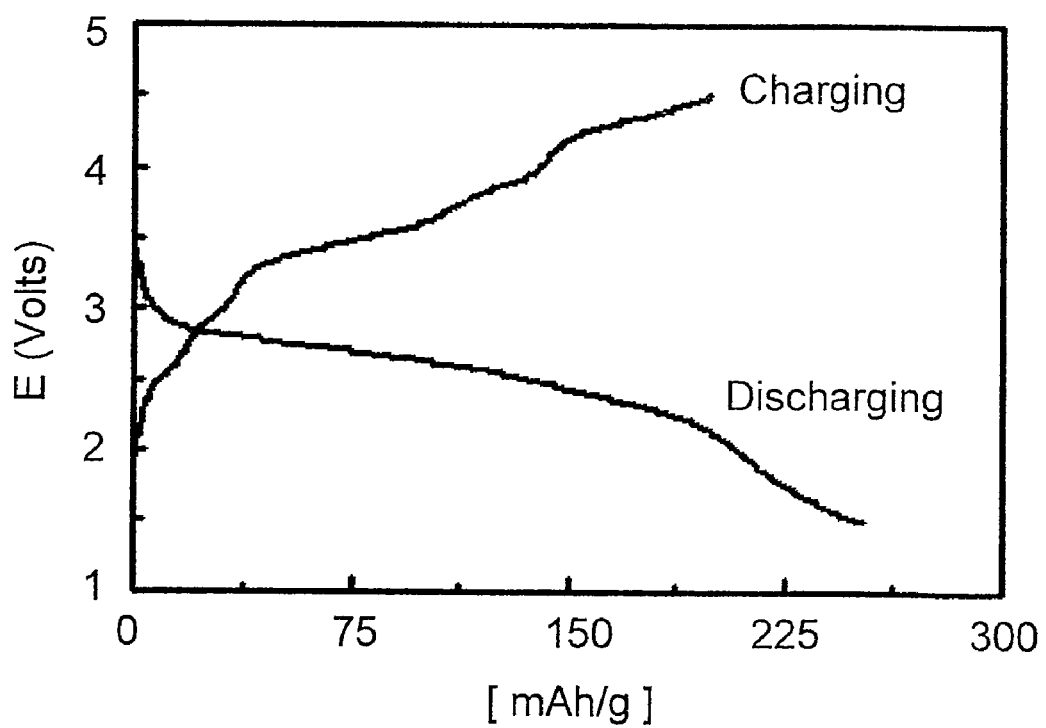
FIG. 5 is a charge-discharge curve of a coin battery fabricated in Test Example 4.

A test was performed in the same manner as in Test Example 2 except that the phenanthrenequinone compound (1b-2) was used as the electrode active material in place of the phenanthrenequinone compound (1b-1). The results are shown in FIG. 5. FIG. 5 is a charge-discharge curve of the coin battery of the present invention. FIG. 5 confirmed that in the coin battery of the present invention, which is one of the batteries using lithium ions as a mobile carrier, reversible charge/discharge reaction proceeds. Thereafter, the charge/discharge cycle test was repeated to a total of 5 cycles, during which no significant deterioration in capacity was observed.

Test Example 5

The light absorption characteristics and the fluorescence properties of the phenanthrenequinone compounds were evaluated.

In the measurements of UV-visible spectrum and fluorescence spectrum, chloroform was used as a solvent, and the UV-visible spectrum and the fluorescence spectrum were measured at a concentration of $1.0\times10^{-5}$ mol and $1.0\times10^{-6}$ mol, respectively. For the measurement of UV-visible spectrum, a spectrophotometer (trade name: SHIMADZU UV-2500PC UV-VIS, available from Shimadzu Corporation) was used. For the measurement of fluorescence spectrum, a spectrofluorometer (trade name: HORIBA jobin Yvon SPEX FluoroMax-3, available from Horiba, Ltd.) was used.

The result showed that the maximum absorption wavelengths in the UV-visible spectra of the dimer and the trimer of 9,10-bis(t-butyldimethylsilyloxy)-2-iodo-9,10-dihydrophenanthrene were 300 nm and 318 nm, respectively. From comparison with the maximum absorption wavelength of the monomer of 260 nm obtained under the exact same measurement conditions, it is observed that the maximum absorption wavelength was shifted toward the long wavelength side, due to the extension of the conjugated π system.

Further, in the fluorescence spectra, the maximum emission wavelengths of the dimer and the trimer of 9,10-bis(t-butyldimethylsilyloxy)-2-iodo-9,10-dihydro-phenanthrene were 425 nm and 437 nm, respectively, and the shift toward the long wavelength side was also observed. The excitation wavelengths in this case correspond to the respective maximum absorption wavelengths in the UV-visible spectra. The maximum emission wavelength of the monomer is 395 nm.

Based on the foregoing results, it is confirmed that the dimer and the trimer of 9,10-bis(t-butyldimethylsilyloxy)-2-iodo-9,10-dihydro-phenanthrene have fluorescence properties.

INDUSTRIAL APPLICABILITY

According to the present invention, it is possible to provide a power storage device having a high output, a small weight, and a high capacity. In short, the power storage device of the present invention is suitably used as a power source for various portable electronic equipment, transportation equipment, uninterruptive power supplies, and the like.

The invention claimed is:

1. An electrode active material comprising a phenanthrenequinone compound represented by the general formula (I):

[Chemical formula 1]

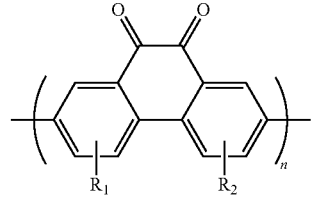

(1)

wherein $R_1$ and $R_2$ are each a hydrogen atom; n is an integer of two or more; and each terminal bond is a hydrogen bond.

2. The electrode active material in accordance with claim 1, wherein, in the general formula (1), n is two or three.

3. The electrode active material in accordance with claim 1 is a positive electrode material.

4. A power storage device comprising a positive electrode, a negative electrode, and an electrolyte, and converting an electron transfer associated with a redox reaction into an electric energy, wherein
at least one selected from the positive electrode and the negative electrode includes the electrode active material of claim 1.

5. The power storage device in accordance with claim 4, wherein the electrolyte comprises a lithium cation.

* * * * *